US012765782B2

(12) United States Patent
Brauer et al.

(10) Patent No.: US 12,765,782 B2
(45) Date of Patent: Oct. 20, 2026

(54) DEVICES, SYSTEMS, AND METHODS FOR DISPLAYING STENOSIS MEASUREMENTS AND CALCULATIONS

(71) Applicant: Canon U.S.A., Inc., Melville, NY (US)

(72) Inventors: Jacob Schieffelin Brauer, Cambridge, MA (US); Rohini Deb, Boston, MA (US); David Michael Vaccaro, Winchester, MA (US)

(73) Assignee: Canon U.S.A., Inc., Melville, NY (US)

( * ) Notice: Subject to any disclaimer, the term of this patent is extended or adjusted under 35 U.S.C. 154(b) by 685 days.

(21) Appl. No.: 17/512,503

(22) Filed: Oct. 27, 2021

(65) Prior Publication Data

US 2023/0130046 A1 Apr. 27, 2023

(51) Int. Cl.
*A61B 5/02* (2006.01)
*A61B 5/00* (2006.01)

(52) U.S. Cl.
CPC ........ *A61B 5/02007* (2013.01); *A61B 5/0066* (2013.01); *A61B 5/6852* (2013.01); *A61B 5/742* (2013.01)

(58) Field of Classification Search
CPC . A61B 5/0066; A61B 5/02007; A61B 5/0084; A61B 5/742; A61B 5/743; A61B 5/6852
See application file for complete search history.

(56) References Cited

U.S. PATENT DOCUMENTS 5,327,398 A * 7/1994 Wansley ................. G01S 15/96 367/111
6,049,465 A * 4/2000 Blish, II .................. H01L 24/73 257/E23.079

(Continued)

FOREIGN PATENT DOCUMENTS

EP 2742858 A2 6/2014

OTHER PUBLICATIONS

Optis Software Instructions for Use, St. Jude Medical, Jan. 2017.

(Continued)

*Primary Examiner* — Charles A Marmor, II
*Assistant Examiner* — Andrew E Hoffpauir
(74) *Attorney, Agent, or Firm* — Canon U.S.A., Inc. IP Division

(57) ABSTRACT

Devices, systems, and methods calculate a first stenosis measurement of a measured location in a lumen based on optical-imaging data of the lumen, on the measured location in the lumen, and on a first reference location in the lumen; and generate a screen that includes a tomographic view of the lumen, a longitudinal view of the lumen, and the first stenosis measurement, wherein the tomographic view of the lumen and the longitudinal view of the lumen are based on the optical-imaging data of the lumen, wherein the tomographic view includes a tomographic-view measured-location indicator that indicates the measured location in the lumen and a first tomographic-view reference indicator that indicates the first reference location in the lumen, and wherein the longitudinal view includes a longitudinal-view measured-location indicator that indicates the measured location in the lumen and a first longitudinal-view reference indicator that indicates the first reference location in the lumen.

20 Claims, 9 Drawing Sheets

(56) References Cited

U.S. PATENT DOCUMENTS

| | | | | |
|---|---|---|---|---|
| 7,916,157 | B1 * | 3/2011 | Kelley | G06F 3/0481 345/660 |
| 8,306,522 | B1 * | 11/2012 | Delker | G06F 21/577 455/418 |
| 9,138,147 | B2 | 9/2015 | Schmitt et al. | |
| 9,572,495 | B2 | 2/2017 | Schmitt et al. | |
| 2003/0158687 | A1 * | 8/2003 | Nygaard, Jr. | G01R 13/029 702/117 |
| 2003/0171894 | A1 * | 9/2003 | Giovanni Battista Mancini | A61B 5/02007 702/182 |
| 2009/0132232 | A1 * | 5/2009 | Trefler | G06Q 10/10 704/8 |
| 2011/0071404 | A1 | 3/2011 | Schmitt et al. | |
| 2011/0081057 | A1 * | 4/2011 | Zeng | G06T 7/11 382/128 |
| 2012/0065511 | A1 * | 3/2012 | Jamello, III | A61B 8/465 600/443 |
| 2012/0137283 | A1 * | 5/2012 | Antill | G06F 8/60 717/178 |
| 2013/0072805 | A1 | 3/2013 | Schmitt et al. | |
| 2014/0276011 | A1 * | 9/2014 | Schmitt | A61B 5/0066 600/425 |
| 2014/0378850 | A1 * | 12/2014 | Plakas | G06T 7/0012 600/504 |
| 2016/0335766 | A1 * | 11/2016 | Ambwani | G06T 7/11 |
| 2019/0029625 | A1 * | 1/2019 | Zhong | A61B 8/12 |
| 2019/0102906 | A1 | 4/2019 | Kunio | |
| 2019/0282182 | A1 * | 9/2019 | Scott | G16H 50/30 |
| 2019/0295731 | A1 * | 9/2019 | Li | G06T 19/20 |
| 2019/0339850 | A1 * | 11/2019 | Ho | A61B 5/7425 |
| 2020/0029861 | A1 * | 1/2020 | Rajguru | A61B 8/469 |

OTHER PUBLICATIONS

Volcano Core Mobile Precision Guided Therapy System Operator's Manual, Volcano Corporation, Nov. 2018.

Ilumien Optis System Instructions for Use, St. Jude Medical, Mar. 2013.

* cited by examiner

DEVICES, SYSTEMS, AND METHODS FOR DISPLAYING STENOSIS MEASUREMENTS AND CALCULATIONS

BACKGROUND

Technical Field

This application generally concerns devices, systems, and methods that perform medical imaging.

Background

Bendable optical-imaging devices (e.g., endoscopes, flexible borescopes) enable the imaging of internal tissues, organs, and structures. For example, in cardiology, a bendable optical-imaging device that is capable of optical coherence tomography (OCT) may be used to acquire depth-resolved images of a sample (e.g., tissues, organs). The bendable optical-imaging device, which may include a flexible body, a coil, and an optical probe, may be navigated through a lumen (e.g., a vessel) or a cavity.

Additionally, imaging catheters may be used to acquire images of regions of stenosis in lumens. The images of the regions of stenosis can be used by medical providers to determine the severity of the stenosis.

SUMMARY

Some embodiments of a medical-imaging device comprise one or more computer-readable media storing instructions, and one or more processors that are in communication with the one or more computer-readable media. And the one or more processors, when executing the instructions, cooperate with the one or more computer-readable media to perform operations that comprise: calculating a first stenosis measurement of a measured location in a lumen based on optical-imaging data of the lumen, on the measured location in the lumen, and on a first reference location in the lumen; and generating a screen that includes a tomographic view of the lumen, a longitudinal view of the lumen, and the first stenosis measurement, wherein the tomographic view of the lumen and the longitudinal view of the lumen are based on the optical-imaging data of the lumen, wherein the tomographic view of the lumen includes a tomographic-view measured-location indicator that indicates the measured location in the lumen and a first tomographic-view reference indicator that indicates the first reference location in the lumen, and wherein the longitudinal view of the lumen includes a longitudinal-view measured-location indicator that indicates the measured location in the lumen and a first longitudinal-view reference indicator that indicates the first reference location in the lumen.

Some embodiments of a method comprise generating a screen that includes a tomographic view of a lumen in a first region of the screen, a longitudinal view of the lumen in a second region of the screen, and a first control for accepting an instruction to calculate a stenosis measurement, wherein the tomographic view of the lumen and the longitudinal view of the lumen are based on optical-imaging data of the lumen; and in response to an activation of the first control, calculating a first stenosis measurement of a measured location in the lumen based on the optical-imaging data of the lumen, on the measured location in the lumen, and on at least one reference location in the lumen, adding the first stenosis measurement to the screen, adding, to the tomographic view of the lumen, a tomographic-view measured-location indicator that indicates the measured location in the lumen and one or more tomographic-view reference indicators that respectively indicate the at least one reference location in the lumen, and adding, to the longitudinal view of the lumen, a longitudinal-view measured-location indicator that indicates the measured location in the lumen and one or more longitudinal-view reference indicators that respectively indicate the at least one reference location in the lumen.

Some embodiments of one or more computer-readable storage media store instructions that, when executed by one or more computing devices, cause the one or more computing devices to perform operations that comprise generating a screen that includes a first control for accepting an instruction to calculate a stenosis measurement and that includes at least one view of a lumen; and in response to an activation of the first control, calculating a first stenosis measurement of a measured location in the lumen based on the optical-imaging data of the lumen, on the measured location in the lumen, and on at least one reference location in the lumen, and adding the first stenosis measurement to the screen, wherein the at least one view of the lumen is based on optical-imaging data of the lumen, and wherein the at least one view of the lumen includes a measured-location indicator that indicates the measured location in the lumen.

DESCRIPTION

Figure 1:
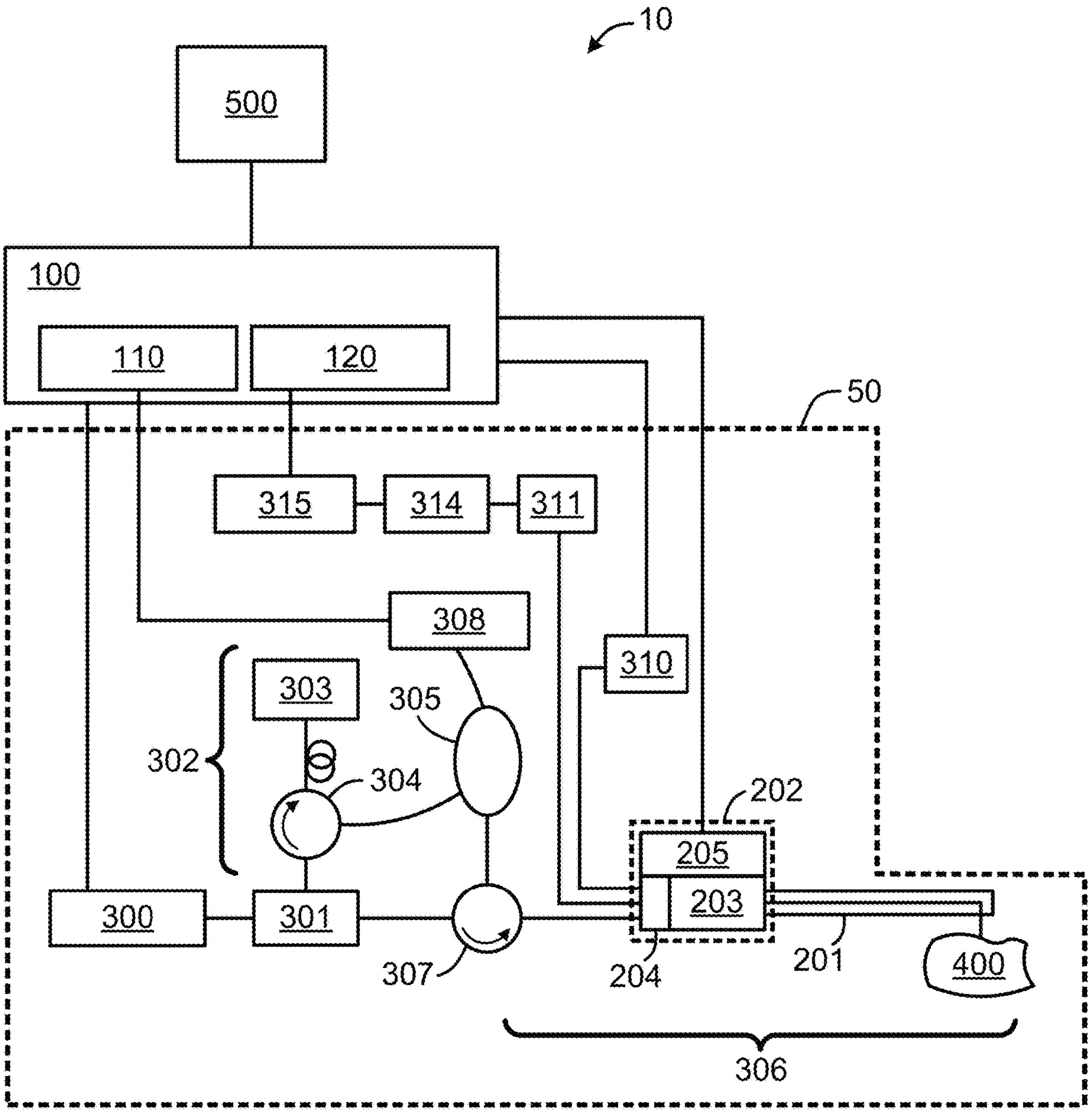
FIG. 1 illustrates an example embodiment of a medical-imaging system.

The following paragraphs describe certain explanatory embodiments. Other embodiments may include alternatives, equivalents, and modifications. Additionally, the explanatory embodiments may include several novel features, and a particular feature may not be essential to some embodiments of the devices, systems, and methods that are described herein. Furthermore, some embodiments include features from two or more of the following explanatory embodiments.

Also, as used herein, the conjunction "or" generally refers to an inclusive "or," although "or" may refer to an exclusive "or" if expressly indicated or if the context indicates that the "or" must be an exclusive "or." Furthermore, as used herein, the terms "first," "second," and so on, do not necessarily denote any ordinal, sequential, or priority relation, but are used to more clearly distinguish one member, operation, element, or set from another, unless specified otherwise.

And, in the following description and in the drawings, like reference numerals designate identical or corresponding members throughout the several views.

FIG. 1 is a schematic of an example embodiment of a medical-imaging system. The medical-imaging system 10 includes an imaging subsystem 50; an imaging station 100, which is a specially-configured computing device (e.g., desktop, laptop, server, workstation); and a display device 500. The imaging subsystem 50 includes a bendable optical-imaging device 201, a patient interface unit (PIU) 202, an OCT-light source 300, a splitter 301, a mirror 303, a first circulator 304, an OCT combiner 305, a second circulator 307, an OCT detector 308, an excitation-light source 310, a dichroic filter 311, a line filter 314, and a fluorescence detector 315. And the imaging station 100 includes an OCT-processing unit 110 and a fluorescence-processing unit 120.

This embodiment of the medical-imaging system 10 is a multi-modal optical coherence tomography (MMOCT) system (e.g., a multi-modality swept-source OCT system). Although this embodiment of the medical-imaging system 10 can perform both OCT imaging and fluorescence imaging (e.g., auto-fluorescence imaging, near-infrared auto-fluorescence imaging, fluorescence-lifetime imaging), some embodiments of the medical-imaging system 10 perform other modalities of imaging (e.g., near infrared spectroscopy (NIRS)) in addition to fluorescence imaging and OCT imaging or in alternative to either or both of fluorescence imaging and OCT imaging.

In FIG. 1, the bendable optical-imaging device 201 includes a tubular flexible body (e.g., a catheter) that surrounds an optical probe. The tubular flexible body may be referred to herein as a "flexible body." Some embodiments of the bendable optical-imaging device 201 include one or more optical fibers (e.g., a single clad fiber, a double clad fiber (DCF)) with a polished ball lens at the tip thereof for side-view scanning. The distal optics of the bendable optical-imaging device 201 may also include a DCF, a GRIN lens, or a refractive element (e.g., grating). The bendable optical-imaging device 201 can perform optical-scanning procedures inside a lumen (e.g., vessel, bronchus, intestine, trachea, ear canal), cavity (e.g., stomach, nasal cavity), or other structure.

Figure 2A:
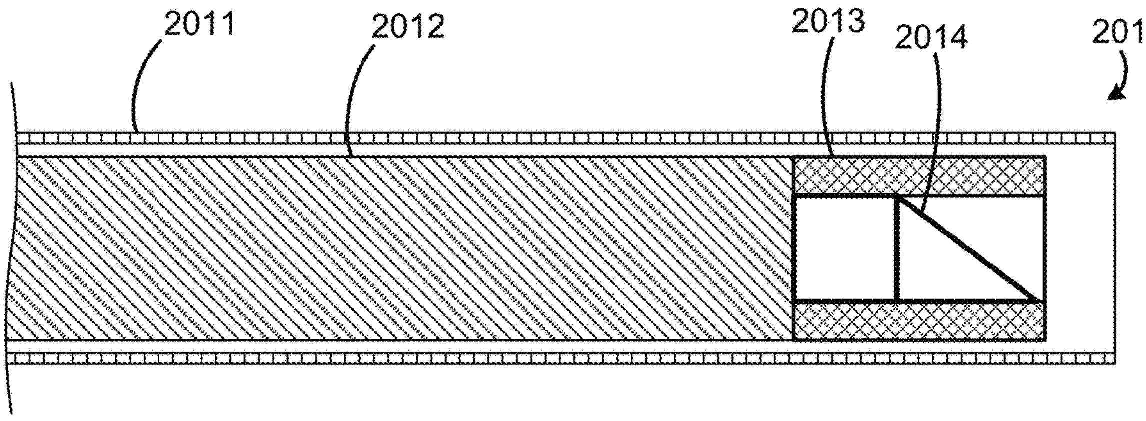
FIGS. 2A-2B illustrate an example embodiment of a bendable optical-imaging device.
Figure 2B:
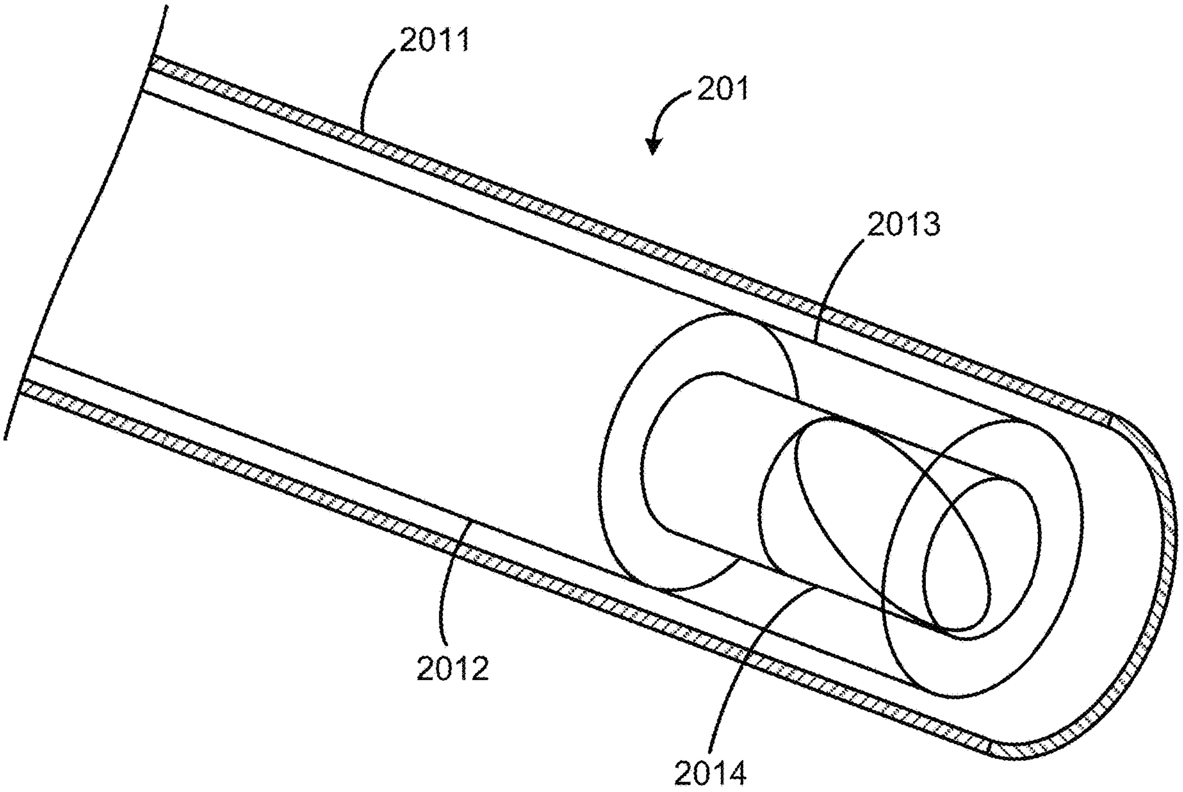

For example, FIGS. 2A-B illustrate an example embodiment of a bendable optical-imaging device. FIG. 2A illustrates a partially cutaway side view of the bendable optical-imaging device 201, and FIG. 2B illustrates a partially cutaway perspective view of the bendable optical-imaging device 201. The bendable optical-imaging device 201 includes a tubular flexible body 2011, a coil 2012, a protector 2013, and an optical probe 2014.

As shown in FIG. 1, the bendable optical-imaging device 201 may be connected to the PIU 202, which can spin the coil 2012, for example during a pullback procedure. The coil 2012 delivers torque from its proximal end to its distal end. In some embodiments, the coil 2012 is fixed with, or to, the optical probe 2014 such that a distal end of the optical probe 2014 also spins with the coil 2012, which provides the optical probe 2014 with a panoramic or multidirectional view. As a beam of light travels through the optical probe 2014, the optical probe 2014 can be rotated, thereby providing the optical probe 2014 with multi-directional views of a surface of interest. Furthermore, the optical probe 2014 (as well as the rest of the bendable optical-imaging device 201) can simultaneously be translated longitudinally during the rotation, which results in a helical scanning pattern. This translation is commonly performed by pulling the distal end of the optical probe 2014 back towards the proximal end and is therefore referred to as a pullback procedure.

In some embodiments, the optical probe 2014 comprises an optical-fiber connector, an optical fiber, and a distal lens. The optical-fiber connector may be used to engage with the PIU 202, and the optical fiber may operate to deliver light to the distal lens and to deliver collected light from the distal lens to the PIU 202. For example, a DCF may transmit and collect OCT light through the core, and the DCF may transmit excitation light and collect Raman and fluorescence light that is reflected by the sample. The distal lens may shape the beam of light, direct illuminating light to the sample, and collect light that is reflected from the sample. The optical probe 2014 may also include a mirror at the distal end that deflects a beam of light outward.

Additionally, the PIU 202 includes a rotary junction 203 (e.g., a fiber-optic rotary junction (FORJ)), a beam combiner 204, and a pullback unit 205. During an optical-scanning procedure, the position of the optical probe 2014 in the bendable optical-imaging device 201, as well as the rest of the bendable optical-imaging device 201, can be adjusted or controlled by the pullback unit 205. Some embodiments of the pullback unit 205 include a rotational motor and a translation motorized stage. In some embodiments, the rotary junction 203 is located in the pullback unit 205. The rotary junction 203 allows the optical probe 2014 to rotate inside the bendable optical-imaging device 201 or relative to the PIU 202. During the rotation, which may be performed by the rotational motor, the optical probe 2014 (as well as the rest of the bendable optical-imaging device 201) can be moved longitudinally (e.g., by a translation motorized stage) so that light (e.g., OCT light, fluorescence light) is collected in a helical scanning pattern. For example, the rotation and translation movements can helically scan the optical probe 2014 inside a lumen and can produce a series of adjacent helical A-scans of the lumen, which can then be used to create a helical two-dimensional (2D) tomogram. Also for example, moving the optical probe 2014 longitudinally within the lumen allows the collection of a series of B-scans, which can be combined to form a three-dimensional (3D) image of the lumen.

The OCT-light source 300 generates OCT light (e.g., with a wavelength of approximately 1.3 μm), which is delivered to a splitter 301. The splitter 301 splits the OCT light into a reference arm 302 and a sample arm 306. The reference arm 302 includes the mirror 303 and the first circulator 304, and the sample arm 306 includes the bendable optical-imaging device 201 and the PIU 202. A reference beam of OCT light transmitted along the reference arm 302 is reflected from the mirror 303, is then transmitted to the first circulator 304, and is then transmitted to the OCT combiner 305. A sample beam of OCT light is transmitted through the second circulator 307, is transmitted along the sample arm 306 (through the one or more optical fibers of the bendable optical-imaging device 201), is incident on a sample 400 (e.g., an organ, tissue), and is reflected or scattered by the sample 400. Some of the reflected or scattered OCT light is collected by the bendable optical-imaging device 201, and the collected OCT light is transmitted through the bendable optical-imaging device 201 (through the one or more optical fibers of the bendable optical-imaging device 201), through the rotary junction 203, through the beam combiner 204 (which may separate the OCT light from the other collected light), and through the second circulator 307 to the OCT combiner 305.

In the OCT combiner 305, the OCT light from the reference arm 302 and the collected OCT light from the sample arm 306 are combined, thereby generating interference patterns. The combined light, which includes the interference patterns, is detected by the OCT detector 308 (e.g., a photodiode, a multi-array camera), which generates an OCT-detection signal that carries OCT-detection data based on the combined light. The OCT-detection signal is supplied to the OCT-processing unit 110 of the imaging station 100. The OCT-processing unit 110 obtains and processes the OCT-detection data.

Additionally, excitation light generated by an excitation-light source 310 is transmitted through the beam combiner 204 to the rotary junction 203, and then to the distal end of the bendable optical-imaging device 201, to illuminate the sample 400. In some embodiments, the excitation light has one of the following wavelengths or wavelength ranges: approximately 0.633 μm, 0.633-0.90 μm, and 0.500-0.700 μm. The excitation light incident on the sample 400 causes the sample 400 to emit fluorescence light. In some embodiments, the fluorescence light emitted by the sample 400 includes autofluorescence light, which is the endogenous fluorescence light that is generated without application of a dye or an agent. And the fluorescence light generated by the sample 400 may include fluorescence light generated by exogenous fluorescence dye or agent in the sample 400.

The bendable optical-imaging device 201 collects fluorescence light (e.g., autofluorescence light), Raman-scattered light, Brillouin-scattered light, and back-reflected excitation light (as well as OCT light) that are emitted or reflected by the sample 400. The one or more optical fibers carry the collected light to the proximal end of the bendable optical-imaging device 201.

After traveling through the beam combiner 204, the fluorescence light emitted from the sample 400, Raman-scattered light, Brillouin-scattered light, and back-reflected excitation light are supplied to a dichroic filter 311, which directs the fluorescence light to the fluorescence detector 315 (e.g., a photomultiplier tube (PMT)).

Also, this embodiment of the imaging subsystem 50 includes a line filter 314 (e.g., a laser line filer). The line filter 314 reduces signal washout from any remaining back-reflected excitation light that reaches the fluorescence detector 315. For example, the line filter 314 can be narrow with a high filtering capability for the NIRAF excitation wavelength (e.g., 635 nm), with only a couple of nanometers of bandwidth, or the bandwidth can be broader (e.g., up more than 2 nm and less than 20 nm or 40 nm) to reduce Raman signals from an optical fiber that can affect NIRAF signal-to-noise ratio.

Based on the received fluorescence light, the fluorescence detector 315 generates a fluorescence-detection signal that carries fluorescence-detection data that include detected values of the fluorescence light (detected fluorescence values). The detected fluorescence values may indicate the intensities of the detected fluorescence light. The fluorescence detector 315 provides the fluorescence-detection signal, which carries the fluorescence-detection data, to the fluorescence-processing unit 120 of the imaging station 100. The fluorescence-processing unit 120 obtains and processes the fluorescence-detection data. In some embodiments, the OCT-detection signal and the fluorescence-detection signal are supplied to the imaging station 100 concurrently or simultaneously.

Based on the detection data (e.g., OCT-detection data, fluorescence-detection data) that is obtained during an optical-scanning procedure, the imaging station 100 generates one or more OCT images, fluorescence images, or multi-modal images (e.g., an OCT-fluorescence image, for example a co-registered OCT-fluorescence image), and the imaging station 100 provides the one or more images to a display device 500, which displays the one or more images. For example, the imaging station 100 may generate a user interface that includes the one or more images and provide the user interface to the display device 500.

Figure 3:
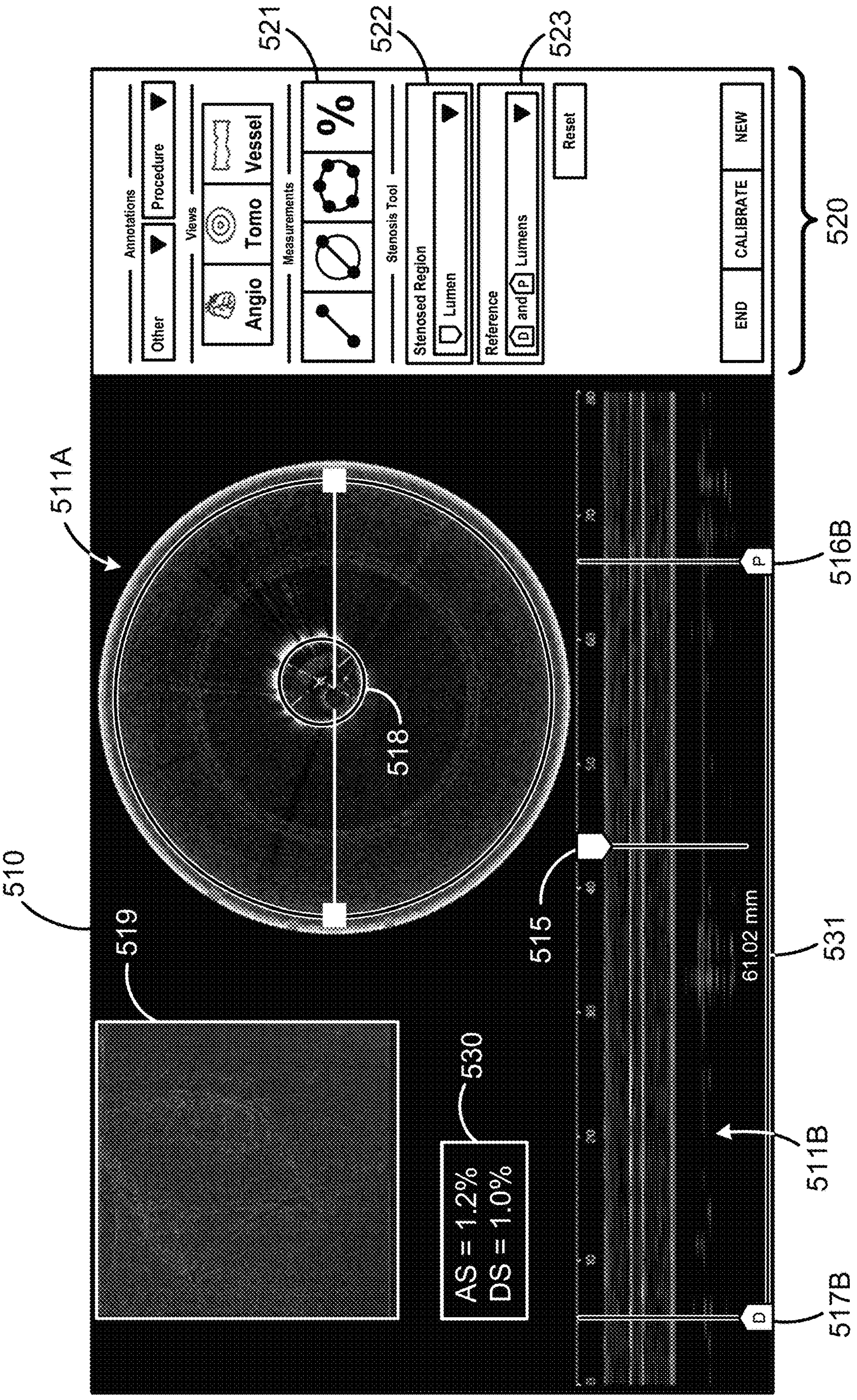
FIG. 3 illustrates an example embodiment of a screen from a user interface.

For example, FIG. 3 illustrates an example embodiment of a screen from a user interface. The screen 510 includes two images 511A-B that were generated based on detection data. Also, the screen includes a control area 520, which includes graphical controls that, when activated, operated, or otherwise manipulated, provide inputs to the user interface. And the screen includes a lumen indicator 518, which indicates the border of a lumen, and an angiogram view 519.

The two images 511A-B include a first image 511A, which shows a tomographic view of a lumen, and a second image 511B, which shows a longitudinal view (which may also be referred to as a vessel view) of the lumen. Additionally, the second image 511B includes a measured-location indicator 515. The measured-location indicator 515 in the second image 511B indicates the measured location in the longitudinal view. The measured location is the location for which one or more stenosis measurements are performed.

Also, the screen 510 includes reference indicators. The reference indicators include a proximal reference indicator 516B and a distal reference indicator 517B. The distal reference indicator 517B indicates the distal reference location in the longitudinal view. And the proximal reference indicator 516B indicates the proximal reference location in the longitudinal view. In some embodiments, the first image 511A also includes a measured-location indicator, a proximal reference indicator, or a distal reference indicator. Furthermore, beneath the second image 511B, the screen 510 also displays the distance 531 between the two reference locations (516B and 517B).

A stenosis measurement indicates a stenosis (e.g., indicates an amount or degree of stenosis) of the lumen (i.e., a narrowing of the lumen). And the imaging station 100 may generate multiple types of stenosis measurements, for example a percent diameter stenosis measurement (% DS) and a percent area stenosis measurement (% AS). A percent diameter stenosis measurement (% DS) indicates the stenosis in terms of the diameter of the lumen at the measured location relative to the diameter of the lumen at one or more reference locations. In some embodiments, a percent diameter stenosis measurement (% DS) can be described by the following:

$$\%DS = 100 \times \frac{D_{ref} - D_m}{D_{ref}}, \tag{1}$$

where $D_{ref}$ is the reference diameter and where $D_m$ is the diameter of the lumen at the measured location. The reference diameter $D_{ref}$ may be the average of the diameter of the lumen at two or more reference locations. For example, in some embodiments the reference diameter $D_{ref}$ can be described by the following:

$$D_{ref} = \frac{D_{distal} + D_{proximal}}{2}, \tag{2}$$

where $D_{distal}$ is the diameter of the lumen at a distal reference location and where $D_{proximal}$ is the diameter of the lumen at a proximal reference location.

Also, a percent area stenosis measurement (% AS) indicates the stenosis in terms of the cross-sectional area of the lumen at the measured location and the cross-sectional area of the lumen at one or more reference locations. In some embodiments, a percent area stenosis measurement (% AS) can be described by the following:

$$\%AS = 100 \times \frac{A_{ref} - A_m}{A_{ref}}, \tag{3}$$

where $A_{ref}$ is the reference area and where $A_m$ is the area of the lumen at the measured location. The reference area $A_{ref}$ may be the average of the area of the lumen at two or more reference locations. For example, in some embodiments the reference area $A_{ref}$ can be described by the following:

$$A_{ref} = \frac{A_{distal} + A_{proximal}}{2}, \tag{4}$$

where $A_{distal}$ is the area of the lumen at a distal reference location and where $A_{proximal}$ is the area of the lumen at a proximal reference location.

The control area 520 includes a stenosis-measurement control 521. When manipulated, the stenosis-measurement control 521 may provide an input that instructs the imaging station 100 to generate one or more stenosis measurements 530. In response to the activation of the stenosis-measurement control 521, the imaging station 100 may add a stenosed-region control 522 and a reference control 523 to the screen 510. In some embodiments, the stenosis-measurement control 521 is a drop-down menu that allows a user to select one or more stenosis measurements 530. For example, the drop-down menu may allow a user to select one or more of a percent diameter stenosis measurement (% DS) and a percent area stenosis measurement (% AS).

The stenosed-region control 522 allows a user to control the selection of the measured location, which is indicated by the measured-location indicator 515. For example, the stenosed-region control 522 may be a drop-down menu. Some embodiments of the drop-down menu offer at least the following options: (a) auto selection, which instructs the imaging station 100 to select the measured location based on the view that is shown in one or both of the images 511A-B; and (b) user selection, which allows a user to select the measured location (e.g., by tapping or clicking a location on one or both of the images 511A-B).

The reference control 523 allows a user to control the selection of the one or more reference locations, which are indicated by respective reference indicators (e.g., the proximal reference indicator 516B, the distal reference indicator 517B). For example, as shown in FIG. 4, the reference control 523 may be a drop-down menu.

Figure 4:
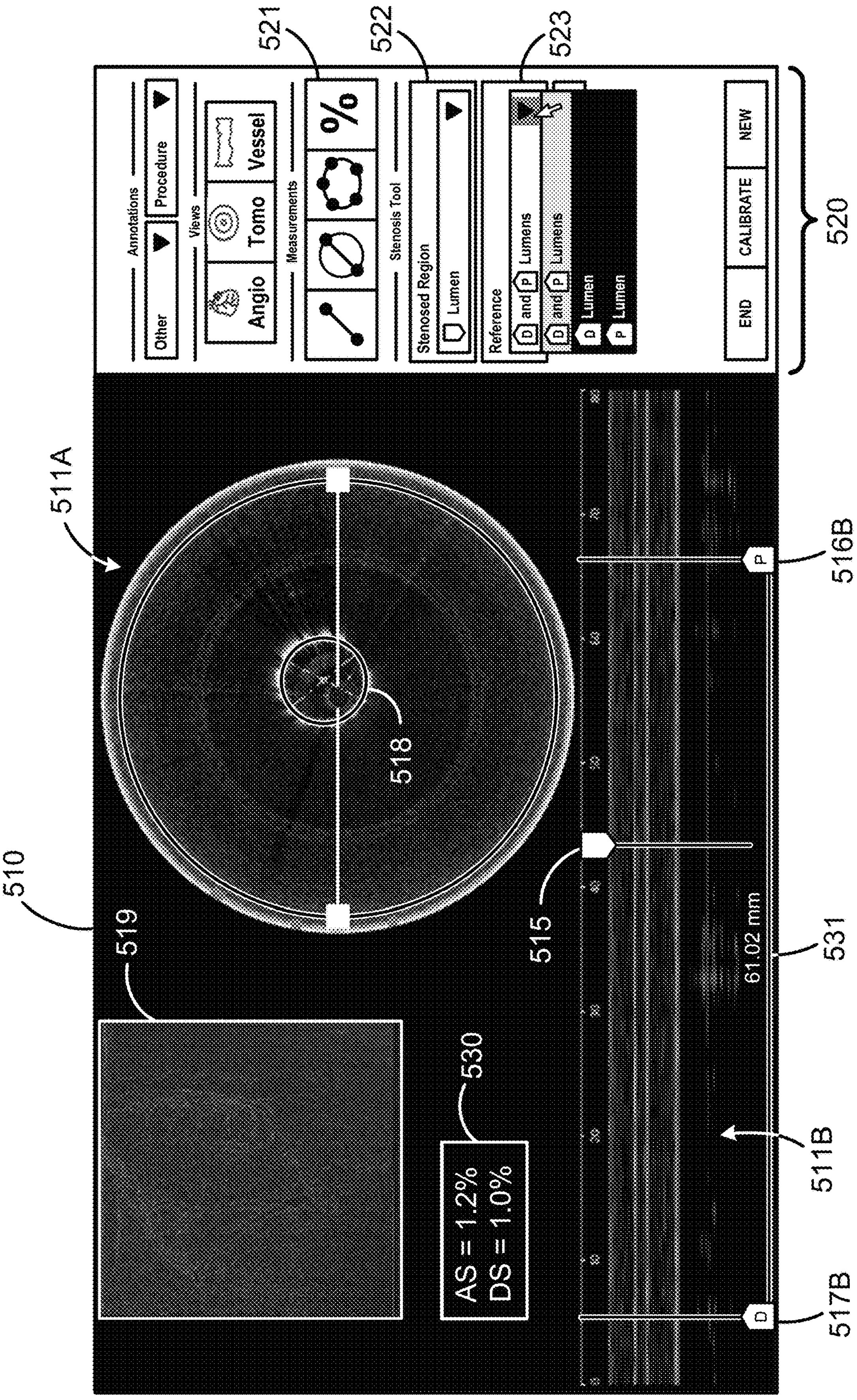
FIG. 4 illustrates an example embodiment of a screen from a user interface.

In the example embodiment in FIG. 4, the reference control 523 is a drop-down menu that has the following options: (a) distal and proximal lumens, (b) distal lumen, and (c) proximal lumen. When (a) distal and proximal lumens has been selected, the imaging station 100 can automatically select both a distal reference location and a proximal reference location, or the imaging station 100 can allow a user to select both a distal reference location and a proximal reference location. For example, a user may select a distal reference location and a proximal reference location by tapping or clicking on selected locations in the tomographic view in the first image 511A or in the longitudinal view in second image 511B.

When (b) distal lumen has been selected, the imaging station 100 can automatically select a distal reference location, or the imaging station 100 can allow a user to select a distal reference location (e.g., by tapping or clicking on selected locations in the tomographic view in the first image 511A or in the longitudinal view in second image 511B).

When (c) proximal lumen has been selected, the imaging station 100 can automatically select a proximal reference location, or the imaging station 100 can allow a user to select a proximal reference location (e.g., by tapping or clicking on selected locations in the tomographic view in the first image 511A or in the longitudinal view in second image 511B).

Thus, without changing the screen 511 of the user interface, the imaging station 100 can display stenosis measurements 530 and receive user inputs (e.g., instructions to adjust one or more parameters, such as the measured location, one or more reference location, the number of stenosis measurements, and the types of stenosis measurements). Accordingly, as shown in FIGS. 3-4, the imaging station 100 can generate a single screen 510 (e.g., a single screen of a GUI) that displays stenosis measurements 530 and that displays controls for adjusting the parameters of the stenosis measurements. Consequently, a user does not need to leave the screen 510 to make changes to the setup of the stenosis measurements, and the user can easily see what features or locations in the images are being used for the measurements. As a result, for the user there are fewer workflow steps, fewer menu items, less confusion about what the measurements measure, fewer misinterpretations, and fewer reasons to study the user manual.

Figure 5:
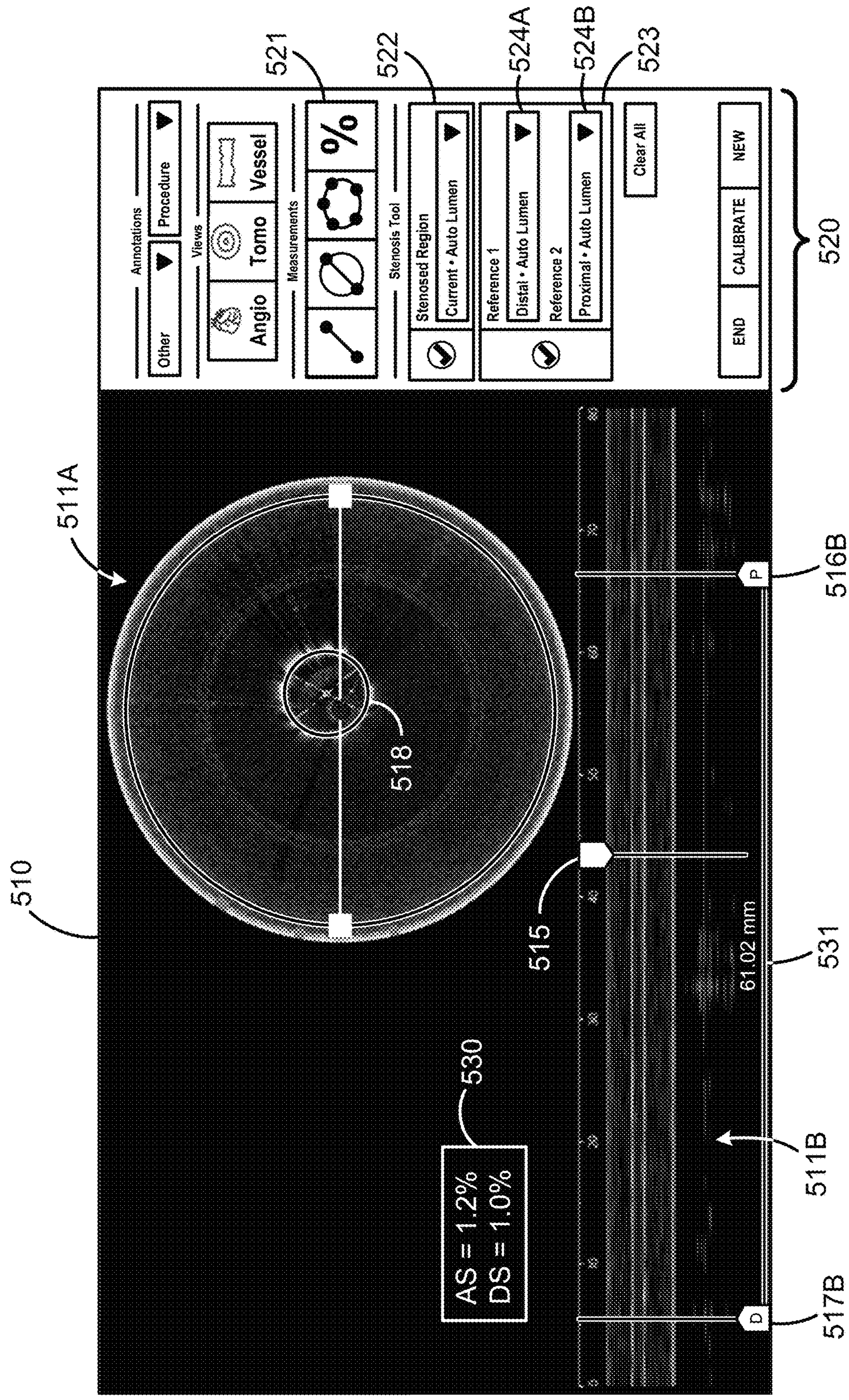
FIG. 5 illustrates an example embodiment of a screen from a user interface.

Furthermore, some embodiments of the screen 510 include different controls than the embodiment that is shown in FIGS. 3-4. For example, FIG. 5 illustrates an example embodiment of a screen from a user interface. The control area 520 in this embodiment includes a stenosed-region control 522 and a reference control 523.

The stenosed-region control 522 is a drop-down menu, which may offer at least the following options: (a) auto selection, and (b) user selection.

The reference control 523 includes two drop-down menus: a distal drop-down menu 524A and a proximal drop-down menu 524B. The distal drop-down menu 524A controls the distal reference location and provides the following options: (a) auto selection, (b) user selection, and (c) none. The proximal drop-down menu 524B controls the proximal reference location and provides the following options: (a) auto selection, (b) user selection, and (c) none. Also, if (c) has been selected for the distal drop-down menu 524A, then (c) is not available in the proximal drop-down menu 524B, and vice versa.

Figure 6:
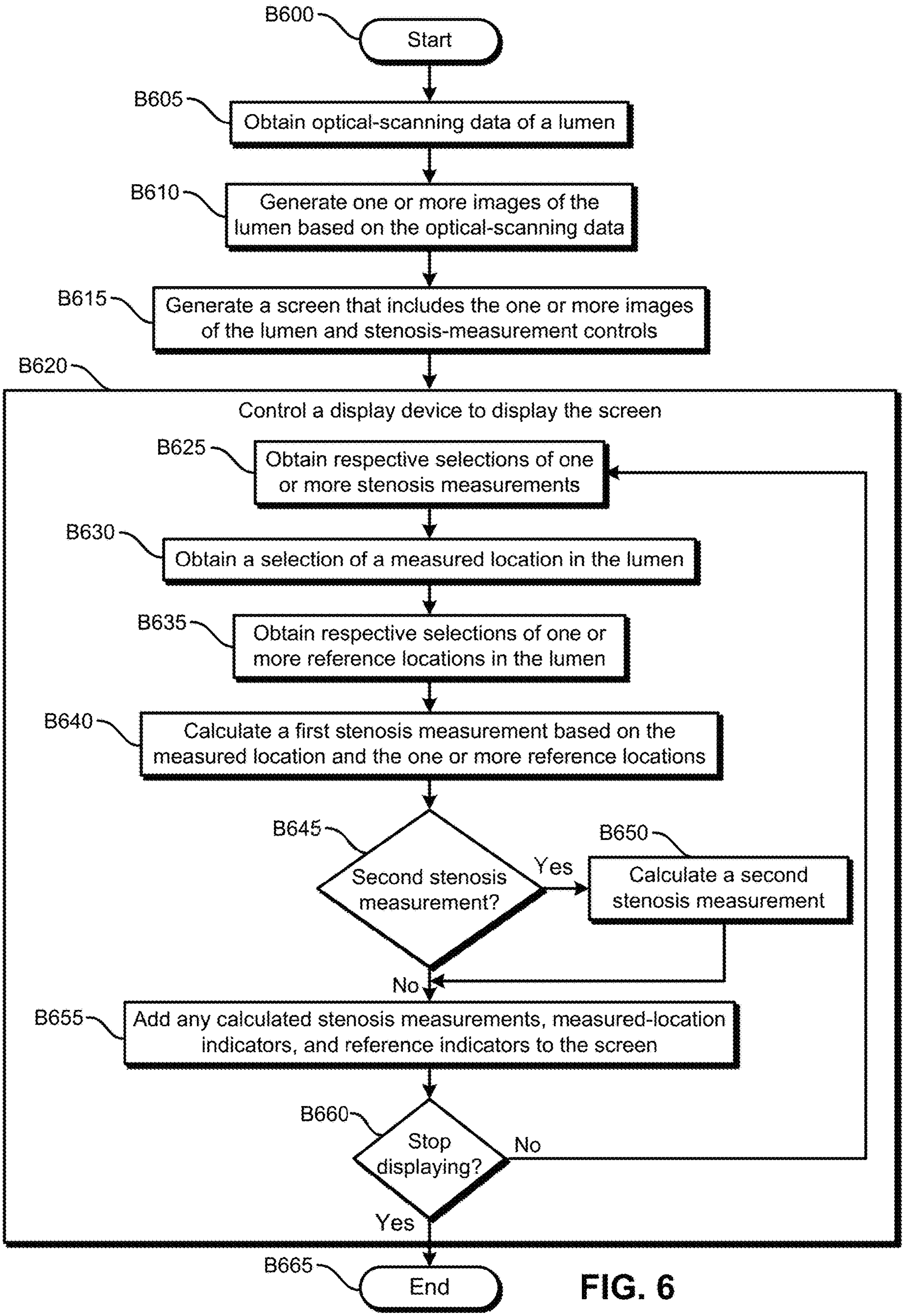
FIG. 6 illustrates an example embodiment of an operational flow for displaying stenosis measurements.

FIG. 6 illustrates an example embodiment of an operational flow for displaying stenosis measurements. Although this operational flow and the other operational flows that are described herein are each presented in a certain order, some embodiments may perform at least some of the operations in different orders than the presented orders. Examples of different orders include concurrent, parallel, overlapping, reordered, simultaneous, incremental, and interleaved orders. And some embodiments of the operational flows may include blocks from two or more of the operational flows that are described herein. Thus, other embodiments of the operational flows that are described herein may omit blocks, add blocks, change the order of the blocks, combine blocks, or divide blocks into more blocks.

Furthermore, although the operational flows that are described herein are performed by an imaging station, some embodiments of these operational flows are performed by two or more imaging stations or by one or more other specially-configured computing devices.

The flow begins in block B600 and moves to block B605, where an imaging station obtains optical-scanning data of a lumen. Next, in block B610, the imaging station generates one or more images of the lumen based on the optical-scanning data. For example, the imaging station may generate an image of a tomographic view of the lumen and an image of a longitudinal view of the lumen. The flow then moves to block B615, where the imaging station generates a screen that includes the one or more images and includes stenosis-measurement controls (e.g., a stenosis-measurement control, a stenosed-region control, a reference control). The flow then moves to block B620, where the imaging station controls a display device to display the screen. Also, while displaying the screen, the imaging station performs blocks B625-B655.

In block B625, the imaging station obtains respective selections of one or more stenosis measurements. For example, the one or more stenosis measurements may include a percent diameter stenosis measurement (% DS) and a percent area stenosis measurement (% AS). The respective selections may be obtained from user operations of one or more stenosis-measurement controls, and the selections may be automatically made by the imaging station.

Next, in block B630, the imaging station obtains a selection of a measured location in the lumen. The selection may be obtained from a user operation (e.g., a tap or a mouse click on a location in one of the one or more images of the lumen), and the selection may be automatically generated by the imaging station.

The flow then advances to block B635, where the imaging station obtains respective selections of one or more reference locations. The selections may be obtained from user operations (e.g., a tap or a mouse click on a location in one of the one or more images of the lumen), and the selections may be automatically generated by the imaging station. Then, in block B640, the imaging station calculates a first stenosis measurement (e.g., a percent diameter stenosis measurement (% DS), a percent area stenosis measurement (% AS)), of the measured location, based on the measured location (e.g., based on the diameter of the lumen at the measured location, based on the area of the lumen at the measured location) and on the one or more reference locations (e.g., based on the diameter of the lumen at the one or more reference locations, based on the area of the lumen at the one or more reference locations).

The flow then proceeds to block B645, where the imaging station determines whether to generate a second stenosis measurement (e.g., whether the one or more stenosis measurements in block B625 include at least two stenosis measurements).

If the imaging station determines to generate a second stenosis measurement (B645=Yes), then the flow moves to block B650. In block B650, the imaging station calculates a second stenosis measurement (e.g., a percent diameter stenosis measurement (% DS), a percent area stenosis measurement (% AS)), of the measured location, based on the measured location (e.g., based on the diameter of the lumen at the measured location, based on the area of the lumen at the measured location) and on the one or more reference locations (e.g., based on the diameter of the lumen at the one or more reference locations, based on the area of the lumen at the one or more reference locations). For example, if the first stenosis measurement is a percent diameter stenosis measurement (% DS), then the second stenosis measurement may be a percent area stenosis measurement (% AS). And, if the first stenosis measurement is a percent area stenosis measurement (% AS), then the second stenosis measurement may be a percent diameter stenosis measurement (% DS). The flow then moves to block B655.

Also, if the imaging station determines not to generate a second stenosis measurement (B645=No), then the flow moves to block B655.

In block B655, the imaging station adds any calculated stenosis measurements, measured-location indicators, and reference indicators to the screen. The flow then proceeds to block B660, where the imaging station determines whether to stop displaying the screen (e.g., whether a stop instruction has been received). If the imaging station determines not to stop displaying the screen (B660=No), then the flow returns to block B625, although in other embodiments the flow may return to block B630 or block B635. If the imaging station determines to stop displaying the screen (B660=Yes), then the flow moves to block B665, where the imaging station stops displaying the screen (e.g., replaces the screen with another screen) and the flow ends.

Figure 7:
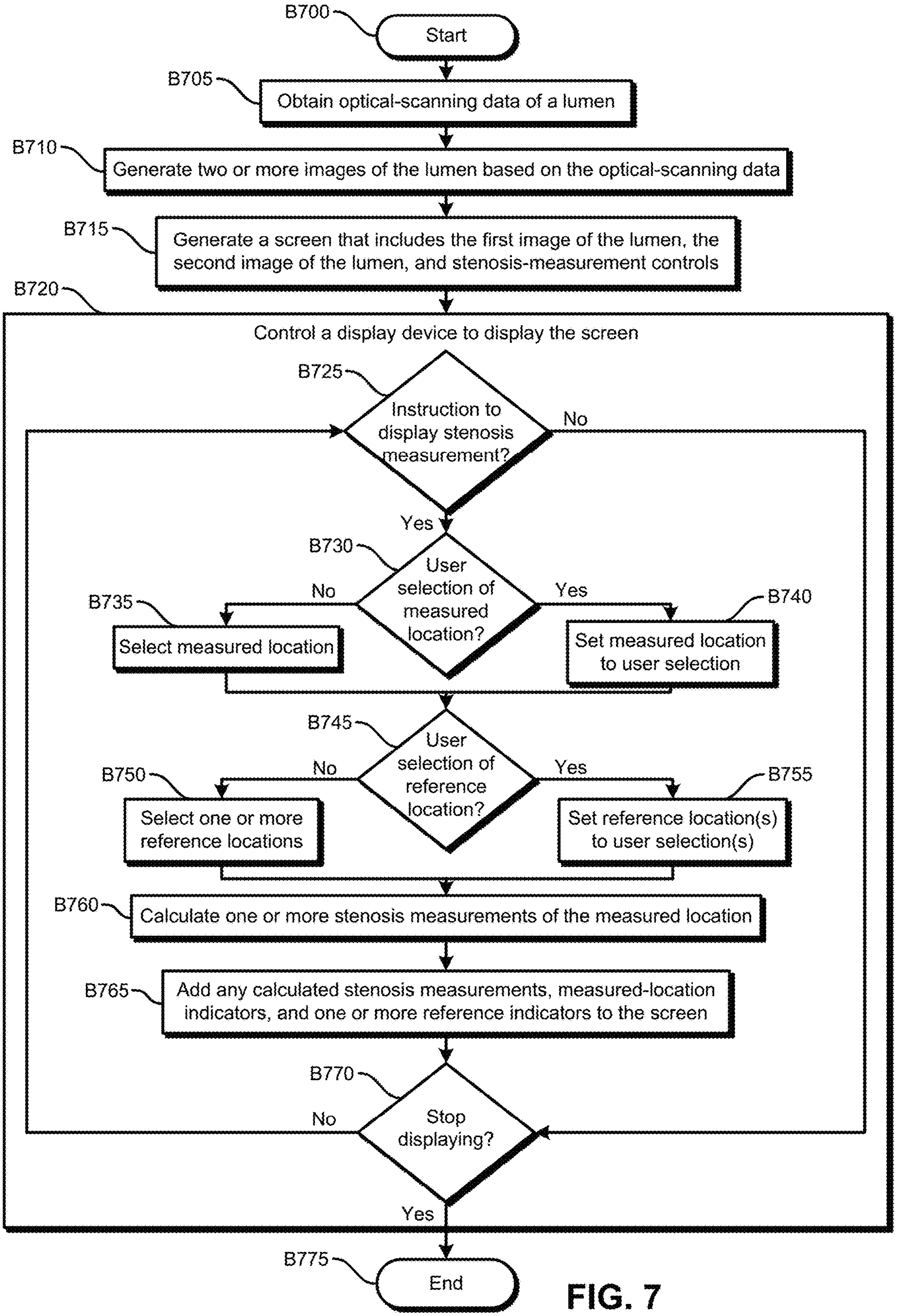
FIG. 7 illustrates an example embodiment of an operational flow for displaying stenosis measurements.

FIG. 7 illustrates an example embodiment of an operational flow for displaying stenosis measurements. The flow begins in block B700 and moves to block B705, where an imaging station obtains optical-scanning data of a lumen. Next, in block B710, the imaging station generates two or more images of the lumen based on the optical-scanning data. The two or more images include at least a first image of the lumen and a second image of the lumen. The flow then moves to block B715, where the imaging station generates a screen that includes the first image of the lumen, the second image of the lumen, and stenosis-measurement controls (e.g., a stenosis-measurement control, a stenosed-region control, a reference control), as well as any other images that were generated in block B710. The flow then moves to block B720, where the imaging station controls a display device to display the screen. Also, while displaying the screen, the imaging station performs blocks B725-B770.

In block B725, the imaging station determines whether it has received an instruction to display one or more stenosis measurements. For example, the imaging station may determine whether a stenosis-measurement control on the screen has been activated to send, to the imaging station, an instruction to display one or more stenosis measurements. If the imaging station determines that it has not received an instruction to display one or more stenosis measurements (B725=No), then the flow proceeds to block B770. If the imaging station determines that it has received an instruction to display one or more stenosis measurements (B725=Yes), then the flow proceeds to block B730.

In block B730, the imaging station determines whether the measured location will be obtained through user selection. For example, the imaging station may determine whether a stenosis-measurement control for the measured location is set to user selection. If the imaging station determines that the measured location will not be obtained through user selection (B730=No), then the flow moves to block B735, where the imaging station selects the measured location, and then the flow advances to block B745. If the imaging station determines that the measured location will be obtained through user selection (B730=Yes), then the flow moves to block B740, where the imaging station sets the measured location according to a user selection of the measured location, and then the flow advances to block B745.

In block B745, the imaging station determines whether one or more reference locations will be obtained through user selection. For example, the imaging station may determine whether a stenosis-measurement control for the one or more reference locations is set to user selection. If the imaging station determines that the one or more reference locations will not be obtained through user selection (B745=No), then the flow moves to block B750, where the imaging station selects the one or more reference locations, and then the flow advances to block B760. If the imaging station determines that the one or more reference locations will be obtained through user selection (B745=Yes), then the flow moves to block B755, where the imaging station sets the one or more reference locations according to respective user selections of the one or more reference locations, and then the flow advances to block B760.

Then, in block B7600, the imaging station calculates one or more stenosis measurements, of the measured location, based on the measured location (e.g., based on the diameter of the lumen at the measured location, based on the area of the lumen at the measured location) and on the one or more reference locations (e.g., based on the diameter of the lumen at the one or more reference locations, based on the area of the lumen at the one or more reference locations).

The flow then moves to block B765, where the imaging station adds any calculated stenosis measurements, one or more measured-location indicators, and one or more reference indicators to the screen. The flow then proceeds to block B770, where the imaging station determines whether to stop displaying the screen (e.g., whether a stop instruction has been received). If the imaging station determines not to stop displaying the screen (B770=No), then the flow returns to block B725, although in other embodiments the flow may return to block B730 or block B745. If the imaging station determines to stop displaying the screen (B770=Yes), then the flow moves to block B775, where the imaging station stops displaying the screen (e.g., replaces the screen with another screen) and the flow ends.

Figure 8:
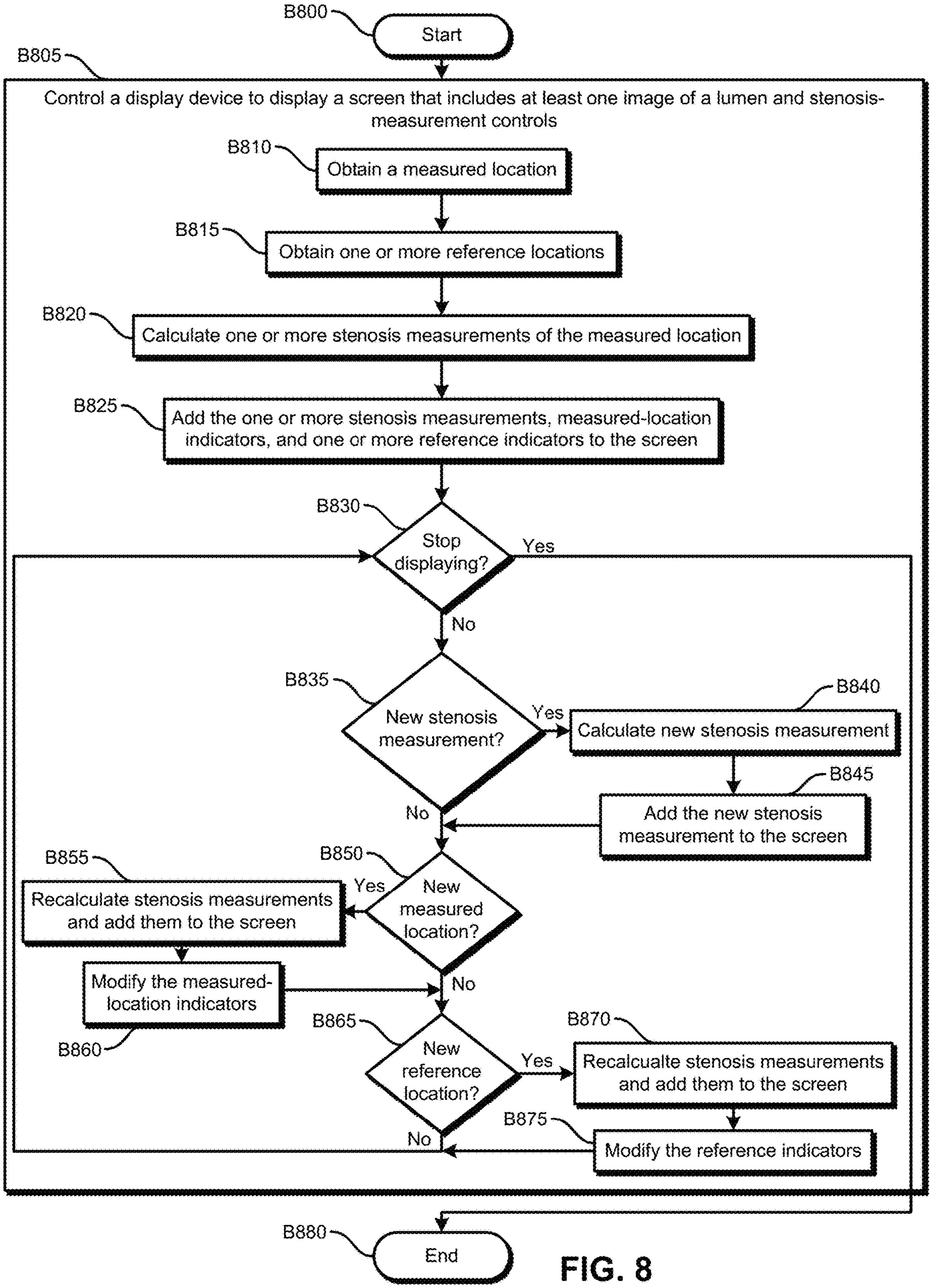
FIG. 8 illustrates an example embodiment of an operational flow for displaying stenosis measurements.

FIG. 8 illustrates an example embodiment of an operational flow for displaying stenosis measurements. The flow begins in block B800 and moves to block B805, where an imaging station generates a screen that includes at least one image of a lumen and stenosis-measurement controls (e.g., a stenosis-measurement control, a stenosed-region control, a reference control), and the imaging station controls a display device to generate the screen. The imaging station may have previously obtained optical-scanning data of the lumen. Also, block B805 includes blocks B810-B875, which are performed while the imaging station controls the display device to display the screen.

In block B810, the imaging station obtains a measured location (e.g., from a user input, from a selection made by the imaging station). Next, in block B815, the imaging station obtains one or more reference locations (e.g., from one or more user inputs, from one or more selections made by the imaging station). The flow then moves to block B820, where the imaging station calculates one or more stenosis measurements of the measured location based on the optical-scanning data, on the measured location, and on the one or more reference locations. The flow then proceeds to block B825, where the imaging station adds the one or more stenosis measurements, one or more measured-location indicators, and one or more reference indicators to the screen.

Then, in block B830, the imaging station determines whether an instruction to stop displaying the screen has been obtained. If the imaging station determines that an instruction to stop displaying the screen has been obtained (B830=Yes), then the imaging station stops displaying the screen (e.g., replaces the screen with another screen), and the flow ends in block B880. If the imaging station determines that an instruction to stop displaying the screen has not been obtained (B830=No), then the flow advances to block B835.

In block B835, the imaging station determines whether to add a new stenosis measurement to the screen. For example, the imaging station may determine to add a new stenosis measurement in response to a user's activation of a control on the screen. Also for example, the imaging station may determine to add a new stenosis measurement when only a percent diameter stenosis measurement (% DS) is included on the screen and the imaging station receives an instruction to add a percent area stenosis measurement (% AS) to the screen in addition to the percent diameter stenosis measurement (% DS), or when only a percent diameter stenosis measurement (% DS) is included on the screen and the imaging station receives an instruction to replace the percent diameter stenosis measurement (% DS) with a percent area stenosis measurement (% AS). Furthermore, the imaging station may determine to add a new stenosis measurement when only a percent area stenosis measurement (% AS) is included on the screen and the imaging station receives an instruction to add a percent diameter stenosis measurement (% DS) to the screen in addition to the percent area stenosis measurement (% AS), or when only a percent area stenosis measurement (% AS) is included on the screen and the imaging station receives an instruction to replace the percent area stenosis measurement (% AS) with a percent diameter stenosis measurement (% DS).

If the imaging station determines not to add a new stenosis measurement to the screen (B835=No), then the flow moves to block B850. If the imaging station determines to add a new stenosis measurement to the screen (B835=Yes), then the flow moves to block B840. In block B840, the imaging station calculates the new stenosis measurement. Then, in block B845, the imaging station adds the new stenosis measurement to the screen. The imaging station may also remove any stenosis measurements that it has been instructed to remove from the screen. The flow then advances to block B850.

In block B850, the imaging station determine whether to change the measured location to a new measured location. For example, the imaging station may determine to change the measured location to a new measured location if a user taps, clicks, or otherwise selects a new measured location, or if a user changes one of the at least one image of the lumen (e.g., scrolls through a tomographic view or a longitudinal view of the lumen) that is displayed on the screen. If the imaging station determines not to change the measured location to a new measured location (B850=No), then the flow advances to block B865. If the imaging station determines to change the measured location to a new measured location (B850=Yes), then the flow moves to block B855.

In block B855, the imaging station recalculates the one or more displayed stenosis measurements, which are calculated based on the new measured location, on the one or more reference locations, and on the optical-scanning data, and the imaging station adds the one or more recalculated stenosis measurements to the screen. Also, the imaging station may remove the previously displayed stenosis measurements. Then, in block B860, the imaging station modifies any measured-location indicators on the screen such that they indicate the new measured location. The flow then proceeds to block B865.

In block B865, the imaging station determines whether to change any of the one or more reference locations to a respective new reference location. For example, the imaging station may determine to change a reference location to a new reference location if a user taps, clicks, or otherwise selects a new reference location, or if a user changes one of the at least one image of the lumen (e.g., scrolls through a tomographic view or a longitudinal view of the lumen) that is displayed on the screen.

If the imaging station determines not to change any of the one or more reference locations to a respective new reference location (B865=No), then the flow returns to block B830. If the imaging station determines to change at least one of the one or more reference locations to a respective new reference location (B865=Yes), then the flow advances to block B870.

In block B870, the imaging station recalculates the one or more displayed stenosis measurements, which are calculated based on the measured location; on the one or more reference locations, which include at least one new reference location and which may include an unchanged reference location; and on the optical-scanning data, and the imaging station adds the one or more recalculated stenosis measurements to the screen. Also, the imaging station may remove the previously displayed stenosis measurements. Then, in block B875, the imaging station modifies the reference indicators on the screen that referred to the previous, but no longer selected, reference location such that they indicate the new reference location. The imaging station may not modify the reference indicators of any unchanged reference locations. The flow then returns to block B830.

Figure 9:
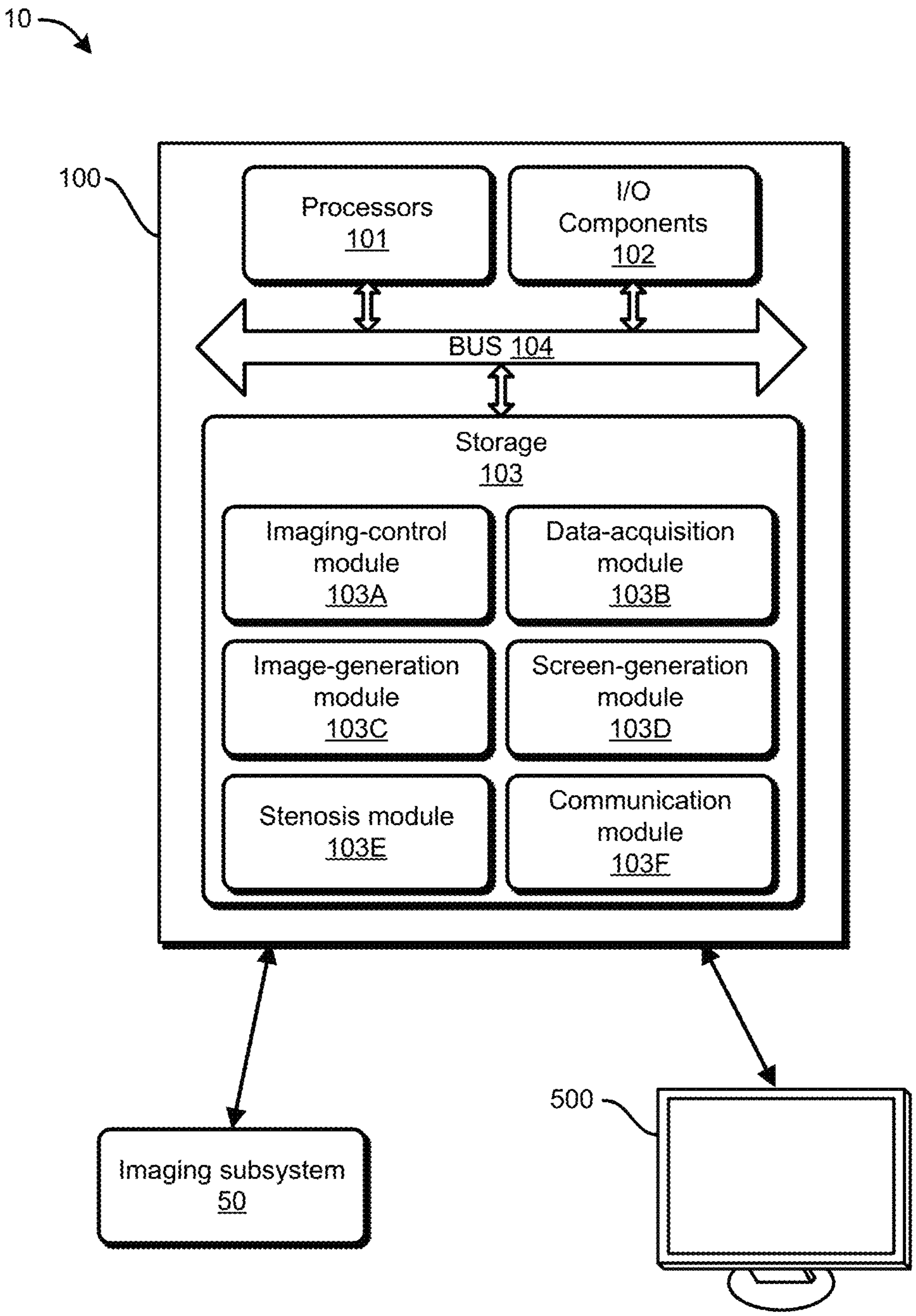
FIG. 9 illustrates an example embodiment of a medical-imaging system.

FIG. 9 illustrates an example embodiment of a medical-imaging system. The medical-imaging system 10 includes an imaging station 100, which is a specially-configured computing device; an imaging subsystem 50; and a display device 500.

The imaging station 100 includes one or more processors 101, one or more I/O components 102, and storage 103. Also, the hardware components of the imaging station 100 communicate via one or more buses 104 or other electrical connections. Examples of buses 104 include a universal serial bus (USB), an IEEE 1394 bus, a PCI bus, an Accelerated Graphics Port (AGP) bus, a Serial AT Attachment (SATA) bus, and a Small Computer System Interface (SCSI) bus.

The one or more processors 101 include one or more central processing units (CPUs), which include microprocessors (e.g., a single core microprocessor, a multi-core microprocessor); one or more graphics processing units (GPUs); one or more application-specific integrated circuits (ASICs); one or more field-programmable-gate arrays (FPGAs); one or more digital signal processors (DSPs); or other electronic circuitry (e.g., other integrated circuits). The I/O components 102 include communication components (e.g., a GPU, a network-interface controller) that communicate with the display device 500, the imaging subsystem 50, a network (not shown), and other input or output devices (not illustrated), which may include a keyboard, a mouse, a printing device, a touch screen, a light pen, an optical-storage device, a scanner, a microphone, a drive, a joystick, and a control pad.

The storage 103 includes one or more computer-readable storage media. As used herein, a computer-readable storage medium refers to a computer-readable medium that includes an article of manufacture, for example a magnetic disk (e.g., a floppy disk, a hard disk), an optical disc (e.g., a CD, a DVD, a Blu-ray), a magneto-optical disk, magnetic tape, and semiconductor memory (e.g., a non-volatile memory card, flash memory, a solid-state drive, SRAM, DRAM, EPROM, EEPROM). The storage 103, which may include both ROM and RAM, can store computer-readable data or computer-executable instructions.

The imaging station 100 additionally includes an imaging-control module 103A, a data-acquisition module 103B, an image-generation module 103C, a screen-generation module 103D, a stenosis module 103E, and a communication module 103F. A module includes logic, computer-readable data, or computer-executable instructions. In the embodiment shown in FIG. 9, the modules are implemented in software (e.g., Assembly, C, C++, C#, Java, BASIC, Perl, Visual Basic). However, in some embodiments, the modules are implemented in hardware (e.g., customized circuitry) or, alternatively, a combination of software and hardware. When the modules are implemented, at least in part, in software, then the software can be stored in the storage 103. Also, in some embodiments, the imaging station 100 includes additional or fewer modules, the modules are combined into fewer modules, or the modules are divided into more modules.

The imaging-control module 103A includes instructions that cause the imaging station 100 to control the operations of the imaging subsystem 50.

The data-acquisition module 103B includes instructions that cause the imaging station 100 to obtain optical-scanning data of a lumen, for example to obtain optical-scanning data of a lumen from the imaging subsystem 50. For example, some embodiments of the data-acquisition module 103B include instructions that cause the imaging station 100 to perform at least some of the operations that are described in block B605 in FIG. 6 and in block B705 in FIG. 7.

The image-generation module 103C includes instructions that cause the imaging station 100 to generate one or more images of lumens based on optical-scanning data. For example, some embodiments of the image-generation module 103C include instructions that cause the imaging station 100 to perform at least some of the operations that are described in block B610 in FIG. 6, in block B710 in FIG. 7, and in block B805 in FIG. 8.

The screen-generation module 103D includes instructions that cause the imaging station 100 to generate screens that include one or more images of lumens, stenosis-measurement controls, calculated stenosis measurements, one or more measured-location indicators, or one or more reference indicators, and to receive inputs from the stenosis-measurement controls. For example, some embodiments of the screen-generation module 103D include instructions that cause the imaging station 100 to perform at least some of the operations that are described in blocks B615-B635 and B655-B660 in FIG. 6; in blocks B715-B730, B740-B745, B755, and B765-B770 in FIG. 7; and in blocks B810-B815, B825-B835, B845-B850, B860-B865, and B875 in FIG. 8.

The stenosis module 103E includes instructions that cause the imaging station 100 to calculate one or more stenosis measurements of measured locations in lumens and, in some embodiments, to select measured locations and reference locations. For example, some embodiments of the stenosis module 103E include instructions that cause the imaging station 100 to perform at least some of the operations that are described in blocks B640-B650 in FIG. 6; in blocks B735, B750, and B760 in FIG. 7; and in blocks B820, B840, B855, and B870 in FIG. 8.

The communication module 103F includes instructions that cause the imaging station 100 to communicate with other computing devices.

The scope of the claims is not limited to the above-described embodiments and includes various modifications and equivalent arrangements.

The invention claimed is:

1. A medical-imaging device comprising:

one or more computer-readable media storing instructions; and one or more processors that are in communication with the one or more computer-readable media and that, when executing the instructions, cooperate with the one or more computer-readable media to perform operations that comprise:

calculating a first dimension of a lumen at a measured location in the lumen based on optical-imaging data of the lumen, wherein the optical-imaging data was acquired from an optical scan that was performed inside the lumen;

calculating a second dimension of the lumen at a first reference location in the lumen based on the optical-imaging data of the lumen;

generating a tomographic view of the lumen and a longitudinal view of the lumen based on the optical-imaging data of the lumen;

generating a screen that includes the tomographic view of the lumen, the longitudinal view of the lumen, a first stenosis measurement, and a first control, wherein the screen simultaneously displays the tomographic view of the lumen, the longitudinal view of the lumen, the first stenosis measurement, and the first control, wherein the longitudinal view of the lumen includes a measured-location indicator that indicates the measured location in the lumen and a first reference indicator that indicates the first reference location in the lumen, and wherein the first control, when activated, displays both a first sub-control and a second sub-control, wherein the first sub-control includes a first indicator that indicates that activation of the first sub-control causes the first stenosis measurement to be calculated based on only one reference location, and the first sub-control, when activated, issues a first instruction to calculate the first stenosis measurement based on a ratio of the first dimension of the lumen at the measured location in the lumen to the second dimension of the lumen at the first reference location in the lumen, and wherein the second sub-control includes a second indicator that indicates that activation of the second sub-control causes the first stenosis measurement to be calculated based on two reference locations, and the second sub-control, when activated, issues a second instruction to calculate the first stenosis measurement based on a ratio of the first dimension of the lumen at the measured location in the lumen to a value that is based on both (i) the second dimension of the lumen at the first reference location in the lumen and (ii) a third dimension of the lumen at a second reference location in the lumen;

in response to the first sub-control issuing the first instruction, calculating the first stenosis measurement based on the ratio of the first dimension of the lumen at the measured location in the lumen to the second dimension of the lumen at the first reference location in the lumen; and in response to the second sub-control issuing the second instruction, calculating the third dimension of the lumen at the second reference location in the lumen based on the optical-imaging data of the lumen, and calculating the first stenosis measurement based on the ratio of the first dimension of the lumen at the measured location in the lumen to the value that is based on both (i) the second dimension of the lumen at the first reference location in the lumen and (ii) the third dimension of the lumen at the second reference location in the lumen.

2. The medical-imaging device of claim 1, wherein the operations further comprise:

in response to the second sub-control issuing the second instruction, adding a second reference indicator that indicates the second reference location in the lumen to the longitudinal view of the lumen.

3. The medical-imaging device of claim 1, wherein the first dimension of the lumen at the measured location is a diameter of the lumen at the measured location, wherein the second dimension of the lumen at the first reference location in the lumen is a diameter of the lumen at the first reference location, wherein the third dimension of the lumen at the second reference location in the lumen is a diameter of the lumen at the second reference location, and wherein the first stenosis measurement is a percent-diameter stenosis measurement.

4. The medical-imaging device of claim 1, wherein the first dimension of the lumen at the measured location is an area of the lumen at the measured location, wherein the second dimension of the lumen at the first reference location in the lumen is an area of the lumen at the first reference location, wherein the third dimension of the lumen at the second reference location in the lumen is an area of the lumen at the second reference location, and wherein the first stenosis measurement is a percent-area stenosis measurement.

5. The medical-imaging device of claim 4, wherein the operations further comprise:

in response to the first sub-control issuing the first instruction, calculating a second stenosis measurement of the measured location in the lumen based on a diameter of the lumen at the measured location in the lumen and on a diameter of the lumen at the first reference location in the lumen, and adding the second stenosis measurement to the screen such that the screen includes both the first stenosis measurement and the second stenosis measurement; and in response to the second sub-control issuing the second instruction, calculating the second stenosis measurement of the measured location in the lumen based on the diameter of the lumen at the measured location in the lumen and a value that is based on both (iii) the diameter of the lumen at the first reference location in the lumen and (iv) a diameter of the lumen at the second reference location in the lumen, and adding the second stenosis measurement to the screen such that the screen includes both the first stenosis measurement and the second stenosis measurement, wherein the second stenosis measurement is a percent-diameter stenosis measurement.

6. The medical-imaging device of claim 1, wherein the operations further comprise:

receiving, via the screen, a user selection of a new measured location; and in response to receiving the user selection of the new measured location, calculating a fourth dimension of the lumen at the new measured location in the lumen based on the optical-imaging data of the lumen, in a case where the first sub-control issued the first instruction more recently than the second sub-control issued the second instruction, calculating a second stenosis measurement of the new measured location based on a ratio of the fourth dimension of the lumen at the new measured location in the lumen to the second dimension of the lumen at the first reference location in the lumen, in a case where the second sub-control issued the second instruction more recently than the first sub-control issued the first instruction, calculating the second stenosis measurement of the new measured location based on a ratio of the fourth dimension of the lumen at the new measured location in the lumen to the value that is based on both (i) the second dimension of the lumen at the first reference location in the lumen and (ii) the third dimension of the lumen at the second reference location in the lumen, replacing the first stenosis measurement on the screen with the second stenosis measurement of the new measured location, modifying the tomographic view of the lumen to show the tomographic view of the new measured location, and modifying the longitudinal view of the lumen by moving the measured-location indicator to the new measured location.

7. The medical-imaging device of claim 1, wherein the operations further comprise:

receiving, via the screen, a user selection of a new reference location; and after receiving the user selection of the new reference location, calculating a fourth dimension of the lumen at the new reference location in the lumen based on the optical-imaging data of the lumen, in a case where the first sub-control issued the first instruction more recently than the second sub-control issued the second instruction, calculating an updated stenosis measurement of the measured location based on a ratio of the first dimension of the lumen at the measured location in the lumen to the fourth dimension of the lumen at the new reference location in the lumen, in a case where the second sub-control issued the second instruction more recently than the first sub-control issued the first instruction, calculating the updated stenosis measurement of the measured location based on a ratio of the first dimension of the lumen at the measured location in the lumen to the value that is based on both (i) the fourth dimension of the lumen at the new reference location in the lumen and (ii) the third dimension of the lumen at the second reference location in the lumen, replacing the first stenosis measurement on the screen with the updated stenosis measurement, and modifying the longitudinal view of the lumen by moving the first reference indicator to the new reference location.

8. The medical-imaging device of claim 1, wherein the value that is based on both (i) the second dimension of the lumen at the first reference location in the lumen and (ii) the third dimension of the lumen at the second reference location in the lumen is an average of (i) the second dimension of the lumen at the first reference location in the lumen and (ii) the third dimension of the lumen at the second reference location in the lumen.

9. A method for medical imaging, the method comprising:

generating a tomographic view of a lumen and a longitudinal view of the lumen based on optical-imaging data of the lumen, wherein the optical-imaging data was acquired from an optical scan that was performed inside the lumen;

generating a screen that includes the tomographic view of the lumen in a first region of the screen, that includes the longitudinal view of the lumen in a second region of the screen, and that includes a first control;

in response to an activation of the first control, displaying both a first sub-control and a second sub-control, wherein the first sub-control includes a first indicator that indicates that activation of the first sub-control causes a first stenosis measurement to be calculated based on only one reference location, and the first sub-control, when activated, issues a first instruction to calculate the first stenosis measurement based on a ratio of a first dimension of the lumen at a measured location in the lumen to a second dimension of the lumen at a first reference location in the lumen, and wherein the second sub-control includes a second indicator that indicates that activation of the second sub-control causes the first stenosis measurement to be calculated based on two reference locations, and the second sub-control, when activated, issues a second instruction to calculate the first stenosis measurement based on a ratio of the first dimension of the lumen at the measured location in the lumen to a value that is based on both (i) the second dimension of the lumen at the first reference location in the lumen and (ii) a third dimension of the lumen at a second reference location in the lumen;

in response to an activation of the first sub-control, calculating the first dimension of the lumen at the measured location in the lumen based on the optical-imaging data of the lumen, calculating the second dimension of the lumen at the first reference location in the lumen based on the optical-imaging data of the lumen, calculating the first stenosis measurement of the measured location in the lumen based on the ratio of the first dimension of the lumen at the measured location in the lumen to the second dimension of the lumen at the first reference location in the lumen, adding the first stenosis measurement to the screen, and adding, to the longitudinal view of the lumen, a measured-location indicator that indicates the measured location in the lumen and a first reference indicator that indicates the first reference location in the lumen, wherein the screen simultaneously displays the tomographic view of the lumen, the longitudinal view of the lumen, the first stenosis measurement, the first control, the measured-location indicator, and the first reference indicator; and in response to an activation of the second sub-control, calculating the first dimension of the lumen at the measured location in the lumen based on the optical-imaging data of the lumen, calculating the second dimension of the lumen at the first reference location in the lumen based on the optical-imaging data of the lumen, calculating the third dimension of the lumen at the second reference location in the lumen based on the optical-imaging data of the lumen, calculating the first stenosis measurement of the measured location in the lumen based on the ratio of the first dimension of the lumen at the measured location in the lumen to the value that is based on both (i) the second dimension of the lumen at the first reference location in the lumen and (ii) the third dimension of the lumen at the second reference location in the lumen, adding the first stenosis measurement to the screen, and adding, to the longitudinal view of the lumen, the measured-location indicator that indicates the measured location in the lumen, the first reference indicator that indicates the first reference location in the lumen, and a second reference indicator that indicates the second reference location in the lumen, wherein the screen simultaneously displays the tomographic view of the lumen, the longitudinal view of the lumen, the first stenosis measurement, the first control, the measured-location indicator, the first reference indicator, and the second reference indicator.

10. The method of claim 9, wherein the first dimension of the lumen at the measured location in the lumen is a diameter of the lumen at the measured location, wherein the second dimension of the lumen at the first reference location in the lumen is a diameter of the lumen at the first reference location, and wherein the third dimension of the lumen at the second reference location in the lumen is a diameter of the lumen at the second reference location.

11. The method of claim 9, wherein the first dimension of the lumen at the measured location in the lumen is an area of the lumen at the measured location, wherein the second dimension of the lumen at the first reference location in the lumen is an area of the lumen at the first reference location, and wherein the third dimension of the lumen at the second reference location in the lumen is an area of the lumen at the second reference location.

12. The method of claim 9, wherein the first control is a drop-down menu, wherein the first sub-control is a respective entry in the drop-down menu, and wherein the second sub-control is a respective entry in the drop-down menu.

13. The method of claim 9, further comprising:

receiving, via the screen, a user selection of a new measured location; and in response to receiving the user selection of the new measured location, calculating a fourth dimension of the lumen at the new measured location in the lumen based on the optical-imaging data of the lumen, replacing, on the screen, the measured-location indicator with an updated measured-location indicator that indicates the new measured location, in a case where the first sub-control issued the first instruction more recently than the second sub-control issued the second instruction, calculating a second stenosis measurement of the new measured location based on a ratio of the fourth dimension of the lumen at the new measured location in the lumen to the second dimension of the lumen at the first reference location in the lumen, in a case where the second sub-control issued the second instruction more recently than the first sub-control issued the first instruction, calculating the second stenosis measurement of the new measured location based on a ratio of the fourth dimension of the lumen at the new measured location in the lumen to the value that is based on both (i) the second dimension of the lumen at the first reference location in the lumen and (ii) the third dimension of the lumen at the second reference location in the lumen, and replacing, on the screen, the first stenosis measurement with the second stenosis measurement.

14. The method of claim 9, wherein the value that is based on both (i) the second dimension of the lumen at the first reference location in the lumen and (ii) the third dimension of the lumen at the second reference location in the lumen is an average of (i) the second dimension of the lumen at the first reference location in the lumen and (ii) the third dimension of the lumen at the second reference location in the lumen.

15. One or more computer-readable storage media storing instructions that, when executed by one or more computing devices, cause the one or more computing devices to perform operations comprising:

generating a tomographic view of a lumen and a longitudinal view of the lumen based on optical-imaging data of the lumen, wherein the optical-imaging data was acquired from an optical scan that was performed inside the lumen;

generating a screen that includes a first control, the tomographic view of the lumen, and the longitudinal view of the lumen, wherein the screen simultaneously displays the first control, the tomographic view of the lumen, and the longitudinal view of the lumen; and in response to an activation of the first control, displaying both a first sub-control and a second sub-control, wherein the first sub-control includes a first indicator that indicates that activation of the first sub-control causes a first stenosis measurement to be calculated based on only one reference location, and the first sub-control, when activated, issues a first instruction to calculate the first stenosis measurement based on a ratio of a first dimension of the lumen at a measured location in the lumen to a second dimension of the lumen at a first reference location in the lumen, and wherein the second sub-control includes a second indicator that indicates that activation of the second sub-control causes the first stenosis measurement to be calculated based on two reference locations, and the second sub-control, when activated, issues a second instruction to calculate the first stenosis measurement based on a ratio of the first dimension of the lumen at the measured location in the lumen to a value that is based on both (i) the second dimension of the lumen at the first reference location in the lumen and (ii) a third dimension of the lumen at a second reference location in the lumen;

in response to an activation of the first sub-control, calculating the first dimension of the lumen at the measured location in the lumen based on the optical-imaging data of the lumen, calculating the second dimension of the lumen at the first reference location in the lumen based on the optical-imaging data of the lumen, calculating the first stenosis measurement of the measured location in the lumen based on the ratio of the first dimension of the lumen at the measured location in the lumen to the second dimension of the lumen at the first reference location in the lumen, adding the first stenosis measurement to the screen, and adding, to the longitudinal view of the lumen, a measured-location indicator that indicates the measured location in the lumen and a first reference indicator that indicates the first reference location in the lumen, wherein the screen simultaneously displays the tomographic view of the lumen, the longitudinal view of the lumen, the first stenosis measurement, the first control, the measured-location indicator, and the first reference indicator; and in response to an activation of the second sub-control, calculating the first dimension of the lumen at the measured location in the lumen based on the optical-imaging data of the lumen, calculating the second dimension of the lumen at the first reference location in the lumen based on the optical-imaging data of the lumen, calculating the third dimension of the lumen at the second reference location in the lumen based on the optical-imaging data of the lumen, calculating the first stenosis measurement of the measured location in the lumen based on the ratio of the first dimension of the lumen at the measured location in the lumen to the value that is based on both (i) the second dimension of the lumen at the first reference location in the lumen and (ii) the third dimension of the lumen at the second reference location in the lumen, adding the first stenosis measurement to the screen, and adding, to the longitudinal view of the lumen, the measured-location indicator that indicates the measured location in the lumen, the first reference indicator that indicates the first reference location in the lumen, and a second reference indicator that indicates the second reference location in the lumen, wherein the screen simultaneously displays the tomographic view of the lumen, the longitudinal view of the lumen, the first stenosis measurement, the first control, the measured-location indicator, the first reference indicator, and the second reference indicator.

16. The one or more computer-readable storage media of claim 15, wherein the operations further comprise:

in response to the activation of the first sub-control, calculating a second stenosis measurement of the measured location in the lumen based on a ratio of a fourth dimension of the lumen at the measured location in the lumen to a fifth dimension of the lumen at the first reference location in the lumen, and adding the second stenosis measurement to the screen such that the screen includes both the first stenosis measurement and the second stenosis measurement; and in response to the activation of the second sub-control, calculating the second stenosis measurement of the measured location in the lumen based on a ratio of the fourth dimension of the lumen at the measured location in the lumen to a value that is based on both (iii) the fifth dimension of the lumen at the first reference location in the lumen and (iv) a sixth dimension of the lumen at the second reference location in the lumen, and adding the second stenosis measurement to the screen such that the screen includes both the first stenosis measurement and the second stenosis measurement.

17. The one or more computer-readable storage media of claim 16, wherein the first stenosis measurement is a percentage of a diameter, and wherein the second stenosis measurement is a percentage of an area.

18. The one or more computer-readable storage media of claim 15, wherein the operations further comprise:

receiving, via the screen, a user selection of a new measured location; and in response to receiving the user selection of the new measured location, calculating a fourth dimension of the lumen at the new measured location in the lumen based on the optical-imaging data of the lumen, replacing, on the screen, the measured-location indicator with an updated measured-location indicator that indicates the new measured location, in a case where the first sub-control issued the first instruction more recently than the second sub-control issued the second instruction, calculating a second stenosis measurement of the new measured location based on a ratio of the fourth dimension of the lumen at the new measured location in the lumen to the second dimension of the lumen at the first reference location in the lumen, in a case where the second sub-control issued the second instruction more recently than the first sub-control issued the first instruction, calculating the second stenosis measurement of the new measured location based on a ratio of the fourth dimension of the lumen at the new measured location in the lumen to the value that is based on both (i) the second dimension of the lumen at the first reference location in the lumen and (ii) the third dimension of the lumen at the second reference location in the lumen, and replacing, on the screen, the first stenosis measurement with the second stenosis measurement.

19. The one or more computer-readable storage media of claim 15, wherein the operations further comprise:

receiving, via the screen, a user selection of a new reference location in the lumen, calculating a fourth dimension of the lumen at the new reference location in the lumen based on the optical-imaging data of the lumen, in a case where the first sub-control issued the first instruction more recently than the second sub-control issued the second instruction, calculating an updated stenosis measurement of the measured location in the lumen based on a ratio of the first dimension of the lumen at the measured location in the lumen to the fourth dimension of the lumen at the new reference location in the lumen, in a case where the second sub-control issued the second instruction more recently than the first sub-control issued the first instruction, calculating the updated stenosis measurement of the measured location based on a ratio of the first dimension of the lumen at the measured location in the lumen to a value that is based on both (iii) the fourth dimension of the lumen at the new reference location in the lumen and (iv) the third dimension of the lumen at the second reference location in the lumen, and replacing, on the screen, the first stenosis measurement with the second updated stenosis measurement.

20. The one or more computer-readable storage media of claim 19, wherein the operations further comprise:

in the longitudinal view of the lumen, moving the first reference indicator to the new reference location in the lumen.

* * * * *